United States Patent [19]

Tsuji et al.

[11] Patent Number: 5,489,514
[45] Date of Patent: * Feb. 6, 1996

[54] DNA CODING FOR GROWTH-INHIBITORY FACTOR AND USE THEREOF

[75] Inventors: Shoji Tsuji, Niigata; Tadashi Miyatake; Yoko Uchida, both of Tokyo; Yasuo Ihara, Yokohama, all of Japan

[73] Assignee: Takeda Chemical Industries, Ltd., Japan

[*] Notice: The portion of the term of this patent subsequent to May 25, 2010, has been disclaimed.

[21] Appl. No.: 924,063

[22] Filed: Aug. 28, 1992

[30] Foreign Application Priority Data

Dec. 13, 1990 [JP] Japan ..................................... 2-410165

[51] Int. Cl.$^6$ ........................... C12P 21/02; C12N 15/12; C12N 1/21; C12N 5/10
[52] U.S. Cl. ................. 435/69.1; 435/91.1; 435/172.3; 435/240.2; 435/252.3; 435/320.1; 536/23.1; 536/23.4; 536/23.5; 536/24.1
[58] Field of Search .............................. 435/6, 69.1, 69.2, 435/69.51, 69.8, 91, 172.1, 172.3, 252.3, 270, 240.2, 320.1; 436/63; 424/570; 514/44, 12; 935/6, 22, 52; 536/23.1, 23.4, 23.5, 24.1, 25.3

[56] References Cited

U.S. PATENT DOCUMENTS

| | | | |
|---|---|---|---|
| 4,828,990 | 5/1989 | Higashi et al. | 435/68.1 |
| 5,214,031 | 5/1993 | Uchida et al. | 514/12 |

OTHER PUBLICATIONS

Vol. 150, No. 3, (1988) Biochemical and Biophysical Research Communications, pp. 1263–1267—Alzheimer's Disease Brain Extract Stimmulates . . . From Neonatal Rats, Uchida, et al.
Brain Research 481 (1989), pp. 190–193, Neurotrophic action of Alzheimer's Disease brain . . . Cortical Neurons, Uchida, et al.

Primary Examiner—Mary E. Mosher
Assistant Examiner—Laurie Scheiner
Attorney, Agent, or Firm—Bierman and Muserlian

[57] ABSTRACT

A novel protein of GIF having growth-inhibitory action, which is present in the brain of normal subjects but absent in the brain of patients with Alzheimer disease, was cloned from a human-cerebral cDNA library and human genomic DNA library. Further, *Escherichia coli* was transformed with a vector integrated by the cDNA to express GIF. The DNA coding for the cloned GIF can be used in the genetic diagnosis and gene therapy for Alzheimer disease, and the expression of the DNA in the transformant can bring about a large production of GIF.

10 Claims, 8 Drawing Sheets

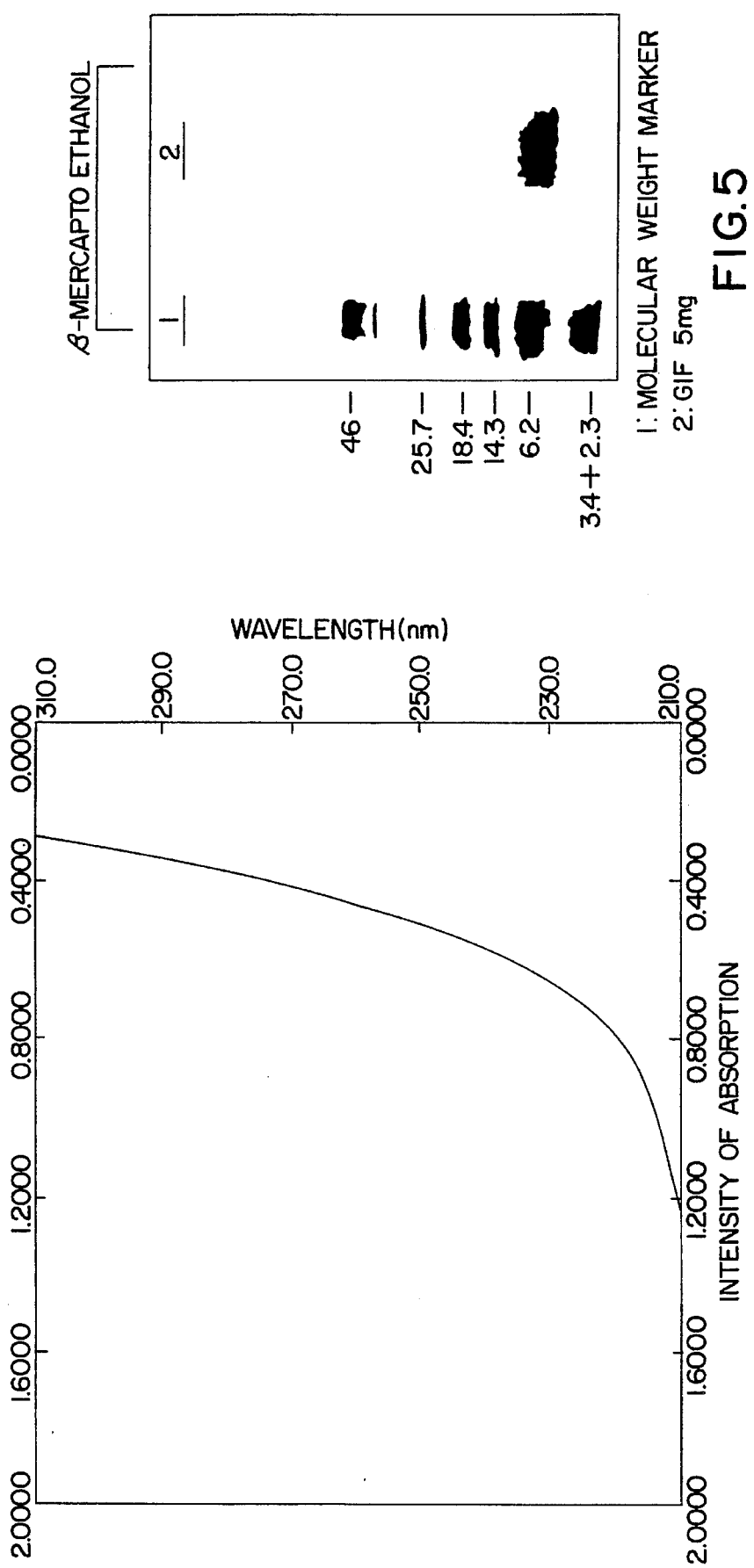

```
CCAGTTGCTT GGAGAAGCCC GTTCACCGCC TCCAGCTGCT GCTCTCCTCG AC ATG        55
                                                         Met
                                                          1

GAC CCT GAG ACC TGC CCC TGC CCT TCT GGT GGC TCC TGC ACC TGC         100
Asp Pro Glu Thr Cys Pro Cys Pro Ser Gly Gly Ser Cys Thr Cys
         5                   10                  15

GCG GAC TCC TGC AAG TGC GAG GGA TGC AAA TGC ACC TCC TGC AAG         145
Ala Asp Ser Cys Lys Cys Glu Gly Cys Lys Cys Thr Ser Cys Lys
             20                  25                  30

AAG AGC TGC TGC TCC TGC TGC CCT GCG GAG TGT GAG AAG TGT GCC         190
Lys Ser Cys Cys Ser Cys Cys Pro Ala Glu Cys Glu Lys Cys Ala
                 35                  40                  45

AAG GAC TGT GTG TGC AAA GGC GGA GAG GCA GCT GAG GCA GAA GCA         235
Lys Asp Cys Val Cys Lys Gly Gly Glu Ala Ala Glu Ala Glu Ala
                     50                  55                  60

GAG AAG TGC AGC TGC TGC CAG TGA G AAGGCACCCC TCCGTGTGGA GCACGT       286
Glu Lys Cys Ser Cys Cys Gln ***
                 65          68

GGAG ATAGTGCCAG GTGGCTCAGT GCCACCTATG CCTGTGTGAA GTGTGGCTGG TGTCC   345
CCTTC CCCTGCTGAC CTTGGAGGAA TGACAATAAA TCCCATGAAC AGCATG            396
```

FIG. 8

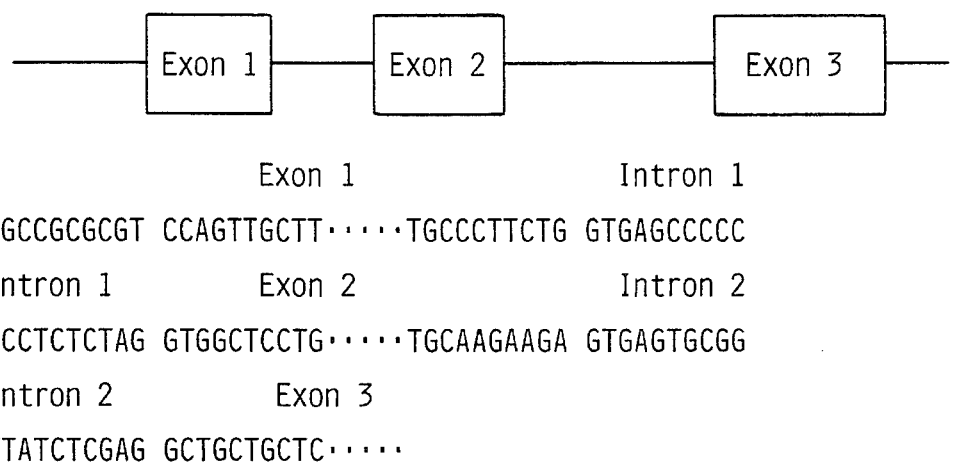

FIG. 9

```
GAATTCTAGA ATGAAGGGGA AGAGAGGCAG GGAAGAGCTG GGAAATACGC AAAGCGCCTT   60
TTTCTCCACT TTCGGAGATG GTACGTGCGC GCTTCCACGC AGTGGCGGCT GCTGCGGCGA  120
GCACGTCCCT GCGGGACCCA CGCGGGGAGT GGGCTGGCAG TCGCGGGATA GCGGCGGCGA  180
GTGGGTCGTG CACGCGGATG CGGGGTCCCA GTGGGGGCGC ACGCGCGGGC GTGGGCGAGC  240
GGGCCCCGGC AGTGCACACA CACGGCAGGG GCGGGGCGAC AGATGCAGTC GTGCGCCGGA  300
GCCCAAGCGC ACAAACGGAA AGAGCGGCCG GTGGCGCAGG GGCGGGCCCC AGCGGGCTTG  360
GCATGCGCGC CCCCGCCCGA GGCTATAAAA GCATCGCCAC CTGCTGCCAC TAGCCAAGCC  420
GCGCGT CCAGTT····                                                  426
       Exon 1
```

FIG. 10

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 68 amino acids
        ( B ) TYPE: Amino acid
        ( C ) STRANDEDNESS: Single
        ( D ) TOPOLOGY: Linear ( i i ) MOLECULE TYPE: protein ( i i i ) HYPOTHETICAL: No ( i v ) ORIGINAL SOURCE:
        ( A ) ORGANISM: human
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE: brain
        ( G ) CELL TYPE:
        ( H ) CELL LINE:
        ( I ) ORGANELLE:

( i x ) FEATURE:
        ( A ) NAME/KEY: GIF
        ( B ) LOCATION:
        ( C ) IDENTIFICATION METHOD:
        ( D ) OTHER INFORMATION:

( x i ) SEQUENCE DESCRIPTION: SEQ ID NO: 1:

```
Met  Asp  Pro  Glu  Thr  Cys  Pro  Cys  Pro  Ser  Gly  Gly  Ser  Cys  Thr  Cys
 1              5                        10                      15

Ala  Asp  Ser  Cys  Lys  Cys  Glu  Gly  Cys  Lys  Cys  Thr  Ser  Cys  Lys  Lys
               20                       25                      30

Ser  Cys  Cys  Ser  Cys  Cys  Pro  Ala  Glu  Cys  Glu  Lys  Cys  Ala  Lys  Asp
          35                       40                  45

Cys  Val  Cys  Lys  Gly  Gly  Glu  Ala  Ala  Glu  Ala  Glu  Ala  Glu  Lys  Cys
     50                       55                  60

Ser  Cys  Cys  Gln
65
```

( 2 ) INFORMATION FOR SEQ ID NO: 2:

( i ) SEQUENCE CHARACTERISTICS:
        ( A ) LENGTH: 204 bp
        ( B ) TYPE: Nucleic acid
        ( C ) STRANDEDNESS: double
        ( D ) TOPOLOGY: Unknown ( i i ) MOLECULE TYPE: cDNA ( i i i ) HYPOTHETICAL: No ( i v ) ORIGINAL SOURCE:
    ( A ) ORGANISM: human
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE: brain
    ( G ) CELL TYPE:
    ( H ) CELL LINE:
    ( I ) ORGANELLE:

( i x ) FEATURE:
    ( A ) NAME/KEY: GIF gene
    ( B ) LOCATION:
    ( C ) IDENTIFICATION METHOD:
    ( D ) OTHER INFORMATION:

( x i ) SEQUENCE DESCRIPTION: SEQ ID NO: 2:

```
ATGGACCCTG AGACCTGCCC CTGCCCTTCT GGTGGCTCCT GCACCTGCGC GGACTCCTGC        60

AAGTGCGAGG GATGCAAATG CACCTCCTGC AAGAAGAGCT GCTGCTCCTG CTGCCCTGCG       120

GAGTGTGAGA AGTGTGCCAA GGACTGTGTG TGCAAAGGCG GAGAGGCAGC TGAGGCAGAA       180

GCAGAGAAGT GCAGCTGCTG CCAG                                              204
```

( 2 ) INFORMATION FOR SEQ ID NO: 3:

( i ) SEQUENCE CHARACTERISTICS:
    ( A ) LENGTH: 426 bp
    ( B ) TYPE: Nucleic acid
    ( C ) STRANDEDNESS: Double
    ( D ) TOPOLOGY: Unknown ( i i ) MOLECULE TYPE: cDNA ( i i i ) HYPOTHETICAL: No ( i v ) ORIGINAL SOURCE:
    ( A ) ORGANISM: human
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE: brain
    ( G ) CELL TYPE:
    ( H ) CELL LINE:
    ( I ) ORGANELLE:

( i x ) FEATURE:
    ( A ) NAME/KEY: Promoter of GIF gene
    ( B ) LOCATION:
    ( C ) IDENTIFICATION METHOD:
    ( D ) OTHER INFORMATION:

( x i ) SEQUENCE DESCRIPTION: SEQ ID NO: 3:

```
GAATTCTAGA ATGAAGGGGA AGAGAGGCAG GGAAGAGCTG GGAAATACGC AAAGCGCCTT        60

TTTCTCCACT TTCGGAGATG GTACGTGCGC GCTTCCACGC AGTGGCGGCT GCTGCGGCGA       120

GCACGTCCCT GCGGGACCCA CGCGGGGAGT GGGCTGGCAG TCGCGGGATA GCGGCGGCGA       180

GTGGGTCGTG CACGCGGATG CGGGGTCCCA GTGGGGGCGC ACGCGCGGGC GTGGGCGAGC       240

GGGCCCCGGC AGTGCACACA CACGGCAGGG GCGGGGCGAC AGATGCAGTC GTGCGCCGGA       300

GCCCAAGCGC ACAAACGGAA AGAGCGGCCG GTGGCGCAGG GGCGGGCCCC AGCGGGCTTG       360

GCATGCGCGC CCCCGCCCGA GGCTATAAAA GCATCGCCAC CTGCTGCCAC TAGCCAAGCC       420

GCGCGT                                                                  426
```

( 2 ) INFORMATION FOR SEQ ID NO: 4:

( i ) SEQUENCE CHARACTERISTICS:
    ( A ) LENGTH: 396 bp
    ( B ) TYPE: Nucleic acid
    ( C ) STRANDEDNESS: Double
    ( D ) TOPOLOGY: Unknown ( i i ) MOLECULE TYPE: cDNA ( i i i ) HYPOTHETICAL: No ( i v ) ORIGINAL SOURCE:
    ( A ) ORGANISM: human
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE: brain
    ( G ) CELL TYPE:
    ( H ) CELL LINE:
    ( I ) ORGANELLE:

( i x ) FEATURE:
    ( A ) NAME/KEY:
    ( B ) LOCATION:
    ( C ) IDENTIFICATION METHOD:
    ( D ) OTHER INFORMATION: GIF gene and flanking sequence ( x i ) SEQUENCE DESCRIPTION: SEQ ID NO: 4:

```
CCAGTTGCTT  GGAGAAGCCC  GTTCACCGCC  TCCAGCTGCT  GCTCTCCTCG  ACATGGACCC      60
TGAGACCTGC  CCCTGCCCTT  CTGGTGGCTC  CTGCACCTGC  GCGGACTCCT  GCAAGTGCGA     120
GGGATGCAAA  TGCACCTCCT  GCAAGAAGAG  CTGCTGCTCC  TGCTGCCCTG  CGGAGTGTGA     180
GAAGTGTGCC  AAGGACTGTG  TGTGCAAAGG  CGGAGAGGCA  GCTGAGGCAG  AAGCAGAGAA     240
GTGCAGCTGC  TGCCAGTGAG  AAGGCACCCC  TCCGTGTGGA  GCACGTGGAG  ATAGTGCCAG     300
GTGGCTCAGT  GCCACCTATG  CCTGTGTGAA  GTGTGGCTGG  TGTCCCCTTC  CCCTGCTGAC     360
CTTGGAGGAA  TGACAATAAA  TCCCATGAAC  AGCATG                                 396
```

( 2 ) INFORMATION FOR SEQ ID NO: 5:

( i ) SEQUENCE CHARACTERISTICS:
        ( A ) LENGTH: 40 bp
        ( B ) TYPE: Nucleic acid
        ( C ) STRANDEDNESS: Double
        ( D ) TOPOLOGY: unknown ( i i ) MOLECULE TYPE: cDNA ( i i i ) HYPOTHETICAL: No ( i v ) ORIGINAL SOURCE:
        ( A ) ORGANISM: human
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE: brain
        ( G ) CELL TYPE:
        ( H ) CELL LINE:
        ( I ) ORGANELLE:

( i x ) FEATURE:
        ( A ) NAME/KEY: Intron 1 of GIF gene
        ( B ) LOCATION:
        ( C ) IDENTIFICATION METHOD:
        ( D ) OTHER INFORMATION:

( x i ) SEQUENCE DESCRIPTION: SEQ ID NO: 5:

```
TGCCCTTCTG  GTGAGCCCCC  CCCTCTCTAG  GTGGCTCCTG                              40
```

( 2 ) INFORMATION FOR SEQ ID NO: 6:

( i ) SEQUENCE CHARACTERISTICS:
    ( A ) LENGTH: 40 bp
    ( B ) TYPE: Nucleic acid
    ( C ) STRANDEDNESS: Double
    ( D ) TOPOLOGY: Unknown ( i i ) MOLECULE TYPE: cDNA ( i i i ) HYPOTHETICAL: No ( i v ) ORIGINAL SOURCE:
    ( A ) ORGANISM: human
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE: brain
    ( G ) CELL TYPE:
    ( H ) CELL LINE:
    ( I ) ORGANELLE:

( i x ) FEATURE:
    ( A ) NAME/KEY: Intron 2 of GIF gene
    ( B ) LOCATION:
    ( C ) IDENTIFICATION METHOD:
    ( D ) OTHER INFORMATION:

( x i ) SEQUENCE DESCRIPTION: SEQ ID NO: 6:

TGCAAGAAGA GTGAGTGCGG TTATCTCGAG GCTGCTGCTC    40

( 2 ) INFORMATION FOR SEQ ID NO: 7:

( i ) SEQUENCE CHARACTERISTICS:
    ( A ) LENGTH: 20 bp
    ( B ) TYPE: Nucleic acid
    ( C ) STRANDEDNESS: Single
    ( D ) TOPOLOGY: Unknown ( i i ) MOLECULE TYPE: Oligonucleotide ( x i ) SEQUENCE DESCRIPTION: SEQ ID NO: 7:

ATGGATCCCG AGACCTGCCC    20

( 2 ) INFORMATION FOR SEQ ID NO: 8:

( i ) SEQUENCE CHARACTERISTICS:
    ( A ) LENGTH: 25 bp
    ( B ) TYPE: Nucleic acid
    ( C ) STRANDEDNESS: Single
    ( D ) TOPOLOGY: Unknown ( i i ) MOLECULE TYPE: Oligonucleotide ( x i ) SEQUENCE DESCRIPTION: SEQ ID NO: 8:

CTGGCAGCAG CAGCTGCACT TTCTC    25

DNA CODING FOR GROWTH-INHIBITORY FACTOR AND USE THEREOF

TECHNICAL FIELD

The present invention relates to a DNA coding for a protein having growth-inhibitory action (referred to as GIF hereinafter), a recombinant vector comprising the DNA, a transformant carrying the vector, and a method for preparing GIF wherein the transformant is cultured in a medium. More particularly, the present invention relates to a recombinant DNA having a promoter region of the GIF gene, a recombinant vector comprising the recombinant DNA and a transformant carrying the recombinant vector.

BACKGROUND ART

Senile dementia has been greatly concerned in a society where many advanced aged persons live, and different efforts have been made of the prevention and therapy for the disease. Particularly, a senile dementia referred to as Alzheimer disease often shows symptoms in the presenile (50 to 60 years), so it is desired to elucidate causes of the disease and to establish the therapy for it.

The obtained findings up to date suggest that Alzheimer disease is an organic disease which has pathological characteristics such as senile blemish and neurotic fiber degeneration, and a clinical characteristic of progressive dementia, and which is involved in enhanced metabolism and abnormal regeneration of neuron.

However, effectively preventive and therapeutic methods for Alzheimer disease have not been found, thereby establishment of them is desired.

DISCLOSURE OF THE INVENTION

The objects of the present invention are an application to genetic diagnosis of Alzheimer disease, and to provide a method for preparing GIF of a novel protein which is useful in the therapy for the disease and a gene coding for the protein in which the gene is applicable for preparation of it. Another object of the present invention is to provide a promoter region of the GIF gene, which is useful in development of the therapeutic agents for the disease.

While having studied substances in the brains of the patients with Alzheimer disease, one of the present inventors have found a substance with growth-inhibitory action to succeed in obtaining GIF, a novel protein, which is present in the brains of normal subjects but becomes to disappear in the brains of the patients with Alzheimer disease.

That is, the protein is an extract per se which is extracted from human brain tissues, or can be collect to purify through combined procedure of ultrafiltration, ion exchange chromatography, gel filtration, high performance liquid chromatography and the like after condensation, for example, practically by the methods of the following Examples.

The thus obtained novel protein of GIF has the following properties.

Molecular weight: about 5,000 (based on SDS polyacrylamide gel electrophoresis)

Form: white, amorphous powder

Stable pH range: 3.0 to 7.7

Heat stability: the growth-inhibitory action is retained by standing at 37° C. for 20 hours or by heating at 100° C. for 5 min.

Physiological activity or growth-inhibitory action of the novel protein, GIF, of the present invention was measured by the following Test examples.

Further, the entire amino acid sequence of the novel protein, GIF, was determined by the methods of the following Examples. Accordingly, the present substance has been found to have the following entire amino acid sequence (SEQ ID NO:1).

Length of the sequence: 68 residues

Type of the sequence: amino acids

Topology: linear (Higher structures, however, are complicated but not linear.)

Kind of sequence: peptide (protein)

Source: an extract from the human brain

Sequence:

| Met 1 | Asp | Pro | Glu | Thr 5 | Cys | Pro | Cys | Pro | Ser 10 |
|---|---|---|---|---|---|---|---|---|---|
| Gly | Gly | Ser | Cys | Thr 15 | Cys | Ala | Asp | Ser | Cys 20 |
| Lys | Cys | Glu | Gly | Cys 25 | Lys | Cys | Thr | Ser | Cys 30 |
| Lys | Lys | Ser | Cys | Cys 35 | Ser | Cys | Cys | Pro | Ala 40 |
| Glu | Cys | Glu | Lys | Cys 45 | Ala | Lys | Asp | Cys | Val 50 |
| Cys | Lys | Gly | Gly | Glu 55 | Ala | Ala | Glu | Ala | Glu 60 |
| Ala | Glu | Lys | Cys | Ser 65 | Cys | Cys | Gln 68 | | |

As shown in the following Test examples, GIF of the novel protein with growth-inhibitory action have been determined to be a useful substance for diagnosis, prevention and therapy for Alzheimer disease. Since the substance, however, is present in the human brain in an extremely small quantity, the substance in this state cannot be practically used.

Thus, the present inventors had thought to find the gene which controlled production of the novel protein, to produce GIF of the novel protein on a large scale by the genetic engineering technique using the gene, and to diagnose, prevent and treat Alzheimer disease using GIF to be largely produced. As a result of intensive study, the present inventors have found the gene (entire DNA) coding for the protein to succeed in determining the DNA sequence.

Isolation of the gene according to the present invention and determination of the DNA sequence can be performed by, for example, the methods of the following Examples.

The thus determined DNA sequence coding for GIF in the human brain (SEQ ID NO:2) is shown as follows.

| | |
|---|---|
| ATG GAC CCT GAG ACC TGC CCC TGC CCT TCT GGT GGC TCC TGC ACC TGC | 48 |
| GCG GAC TCC TGC AAG TGC GAG GGA TGC AAA TGC ACC TCC TGC AAG AAG | 96 |
| AGC TGC TGC TCC TGC TGC CCT GCG GAG TGT GAG AAG TGT GCC AAG GAC | 144 |

| | |
|---|---|
| TGT GTG TGC AAA GGC GGA GAG GCA GCT GAG GCA GAA GCA GAG AAG TGC | 192 |
| AGC TGC TGC CAG | 204 |

A method by which a recombinant vector is prepared, and the vector is transfected to a host to prepare a transformant is illustrated in the following.

Examples of methods by which DNA is integrated to a plasmid include the method described in "Molecular Cloning" [T. Maniatis et al., Cold Spring Harbor Laboratory 239 (1982)] and the like.

A cloned gene can be coupled to the downstream region of the promoter in a vehicle (vector) suitable for expression to obtain an expression recombinant vector.

Examples of the vectors include plasmids derived from Escherichia coli (e.g., pBR322, pBR325, pUC12, pUC13 and the like), plasmids derived from Bacillus subtilis (e.g., pUB110, pTP5, pC194 and the like), plasmids derived from yeast (e.g., pSH19, pSH15 and the like), or bacteriophages such as λ phage, and animal viruses such as retrovirus and vaccinia virus.

The gene has a triplet of ATG as an initiation codon for translation at the 5'-terminus, and may have triplets of TAA, TGA or TAG as termination codons for translation at the 3'-terminus. In order to express the gene a promoter should be coupled to the upstream region of the gene. Any promoters may be used in the the present invention if they are suitable for expression of the gene. Further, T7 promoter, trp promoter, lac promoter, rec A promoter, λ promoter, 1pp promoter and the like are preferably .used in the case where a host to be transformed is a bacterium in Escherichia; SPO1 promoter, SPO2 promoter, penP promoter and the like in the case where a host to be transformed is a bacterium in Bacillus and PHO5 promoter, PGK promoter, GAP promoter, ADH promoter and the like in the case where a host is yeast. More preferably, a bacterium in Escherichia as a host and trp promoter or λ PL promoter as a promoter are used.

In cases where hosts are animal cells, a promoter derived from SV 40, a promoter of retrovirus and the like are used, and more preferably the promoter derived from SV 40 is used.

By using these recombinant vectors which comprise a DNA having the base sequence coding for GIF is prepared a transformant carrying the vector.

Examples of hosts include Escherichia, Bacillus, yeast, animal cells and the like.

Examples of the above mentioned Escherichia include Escherichia coli K12DH1 [Proc. Natl. Acad. Sci. USA 60, 160 (1968)], JM103 [Nucleic Acids Research 9, 309 (1981)], JA221 [Journal of Molecular Biology 120, 517 (1978)], HB101 [Journal of Molecular Biology 41, 459 (1969)], C600 [Genetics 39, 440 (1954)], MM294 [Proc. Natl. Acad. Sci. USA 73, 4174 (1976)] and the like.

Examples of the above mentioned Bacillus include Bacillus subtilis MI114 [Gene 24, 255 (1983)], 207–21 [Journal of Biochemistry 95, 87 (1984)] and the like.

Examples of the above mentioned yeast include Saccharomyces cerevisiae AH22R⁻, NA87-11A, DKD-5D and the like. Examples of the above mentioned animal cells include simian cell COS-7, Vero, Chinese hamster ovary (CHO) cell, mouse L cell, human FL cell and the like.

The above mentioned Escherichia is transformed by the methods described in, for example, Proc. Natl. Acad. Sci. USA 69; 2110 (1972), Gene 17, 107 (1982), and the like.

The Bacillus is transformed by the methods described in, for example, Molecular & General Genetics 168, 111 (1979) and the like.

The yeast is transformed by the method described in, for example, Proc. Natl. Acad. Sci USA 75, 1929 (1978).

The animal cells are transformed by the method described in, for example, Virology 52, 456 (1973).

Thus, a transformant is obtained which carries the recombinant vector comprising DNA having the base sequence coding for GIF.

GIF (SEQ ID NO:1) is produced by culturing the transformant in a medium.

When the transformant of Escherichia or Bacillus as a host is cultured, a liquid medium is preferably used, which contains carbon source, nitrogen source, inorganic compounds and the like to be necessary for growth of the transformant. Examples of carbon source include glucose, dextrin, soluble starch, sucrose and the like; examples of nitrogen source include inorganic or organic components such as ammonium salts, nitric acid salts, corn steep liquor, pepton, casein, meat extract, soybean lees and an extract from potato; and examples of inorganic compounds include calcium chloride, sodium dihydrogenphosphate, magnesium chloride and the like. Further, yeasts, various vitamins, growth-stimulating factors and the like may be supplemented to the medium.

Preferred pH in the medium is about 6 to 8.

For example, M9 medium [Miller, Journal of Experiments in Molecular Genetics, 431–433, Cold Spring Harbor Laboratory, New York (1972)] supplemented with glucose and Casamino acid is preferably used as a medium for culturing Escherichia.

If necessary, for example, agents such as 3β-indol acrylic acid may be added in order to effectively operate a promoter.

When Escherichia is used as a host, culturing of the host can be preformed at a temperature of about 15° C. to 43° C. for about 3 to 24 hours, if necessary, with aeration and stirring.

When Bacillus is used as a host, culturing of the host can be performed at a temperature of about 30° C. to 40° C. for about 6 to 24 hours, if necessary, with aeration and stirring.

When a transformant of yeast as a host is cultured, for example, Burkholder minimum medium [Bostian K. L. et al., Proc. Natl. Acad. Sci. USA 77, 4505 (1980)] is used as a medium. Culturing is usually performed at a temperature of about 20° C. to 35° C. for about 24 to 72 hours, if necessary, with aeration and stirring.

When a transformant of an animal cell as a host is cultured, examples of mediums include MEM [Science, 122, 501 (1952)]supplemented with about 5 to 20% of fetal bovine serum, DMEM [Virology, 8, 396 (1959)], RPMI1640 medium [The Journal of the American Medical Association, 199, 519 (1967)], 199 medium [Proceeding of the Society for the Biological Medicine, 73, 1 (1950)] and the like. Preferred pH is about 6 to 8. Culturing is usually performed at a temperature of about 30° C. to 40° C. for about 15 to 60 hours, if necessary, with aeration and stirring.

Isolation and purification of GIF ( SEQ ID NO:1) from the above mentioned culture can be performed, for example, the methods described below.

The following methods are available: a method that when GIF (SEQ ID NO:1) is extracted from cultured bacteria or cells, after cultured, the bacteria or cells are collected in publicly known manner, and then the desired protein is eluted outside of the bacteria by suspending the collected bacteria or cells in a buffer containing protein denaturants such as guanidine hydrochloride; a method that after destruction of the bacteria of cells by French press, ultrasonification, treatment with lysozyme and/or freeze-thaw, GIF is obtained by centrifugation; and other methods. Among them, a method is preferred in which treatment with lysozyme and ultrasonification are performed together.

GIF ( SEQ ID NO:1) can be purified from the above mentioned supernatant by suitable combinations of the methods for isolation and purification which are publicly known in itself. Examples of these methods for isolation and purification include methods which utilize difference of molecular weights such as a solubility-dependent method using salting out or precipitation, dialysis, ultrafiltration, gel filtration, electrophoresis using SDS-polyacrylamide gel, and the like; methods which utilize difference of electric charge such as ion exchange chromatography; methods which utilize specific affinity such as affinity chromatography; methods which utilize difference of hydrophobicity such as reverse-phase high performance liquid chromatography; methods which utilize difference of isoelectric points such as isoelectric focusing; and other methods.

The thus obtained products are available in the form of dried powder through dialysis and freeze-thaw. Further, adsorption of the products to containers can be preferably prevented by preserving with serum albumin as a carrier.

Coexistence of an extremely small quantity of reducing agents in the purification or preservation process is preferred to prevent oxidation of the products. The reducing agents include β-mercaptoethanol, dithiothreitol, glutathione and the like.

Thus, substantially pure GIF (SEQ ID NO:1) can be obtained which does not substantially contain pyrogen and endotoxin. The products of substantially pure GIF are those containing GIF (SEQ ID NO:1) of 90% (w/w) or more as a protein content, and more preferably those containing GIF of 95% (w/w) or more.

To use GIF (SEQ ID NO:1) of the present invention as pharmaceuticals, the products in the form of powder per se or in the form of pharmaceutical compositions (e.g., injections, tablets, capsules, solutions and ointments) with other pharmaceutically acceptable carriers, fillers and diluents can be orally or parenterally administered safely to homeotherms (e.g., human, mice, rats, hamsters, rabbits, dogs and cats).

Injections are prepared by conventional methods using, for example, physiological saline or aqueous solutions containing glucose and other auxiliaries. Pharmaceutical compositions such as tablets and capsules can be prepared by conventional methods.

When GIF (SEQ ID NO:1) of the present invention is administered as pharmaceuticals, for example, the above mentioned homeotherms receive at a suitable dosage of 1 ng/kg to 100 mg/kg daily in accordance with administration routes, conditions and the like.

Since GIF (SEQ ID NO:1)is produced specifically in the brain of normal subjects, it is suggested that the promoter of the GIF (SEQ ID NO:3) gene operates specifically in the brain. Accordingly, the present inventors cloned the genomic gene of GIF using the cDNA of (SEQ ID NO:4) GIF as a probe in order to obtain the promoter which operates specifically in the brain, and have succeeded in finding the GIF (SEQ OD NO:3) promoter.

In cases where recombinant vectors containing a recombinant DNA having the promoter region of GIF are used, examples of recombinant vectors in which the GIF promoter is integrated, though not limited, include those for animal cells such as pCD vector, CDM8 vector [Aruffo, A. and Seed, B., Proc. Natl. Acad. Sci. USA 84, 8573–8577 (1987)] and retrovirus vector [Cone, R.D. and Mulligan, R.C., Proc. Natl. Acad. Sci. USA 81, 6347–6354 (1984)]; and those for *Escherichia coli* such as pUC [Vieira, J. and Messing, J., Method in Enzymology 153, 3–11 (1987)].

Structural genes which are coupled to the downstream region of the promoter region in recombinant vectors include a structural gene coding for a polypeptide by which functions of various gene products in the brain are elucidated in the central nervous system.

Examples of the gene products include nerve-nutritional factors such as nerve cell growth factor (NGF), basic fibroblast growth factor (basic FGF), acidic fibroblast growth factor (acidic FGF); and other growth factors, lymphokine, and the like.

Reporter genes described below may be used as the above mentioned structural genes. β-Galactosidase gene as well as CAT (chloramphenicol acetyl transferase) gene and alkaline phosphatase gene are widely used as reporter genes, thereby any other genes may be used if the methods for detecting their gene products are available.

In order to integrate the above mentioned structural gene to a vector, the structural gene should be coupled to an appropriate restriction site of the downstream promoter region in the correct direction.

Animal cells, in particular, glia cells and cells of the cranial nervous system are used as hosts which are transformed by the above mentioned recombinant vectors. Egg cells or ES cell [Evans, M. J. and Kaufman, K. H., Nature, 292, 154 (1981)] may be used in a process of DNA transfection to an animal body.

A method using calcium phosphate [Graham, et al., Virology, 52, 456 (1973)], electropolation [Ishizaki, et al., Saibo Kogaku, 5, 557 (1986)], microinjection and the like are used as methods for transforming these cells.

The use of promoters of the present invention can make the cells of the cranial nervous system produce various peptides as the above mentioned.

When oncogenes such as myc and ras as the above mentioned structural genes are used, and the resulting vectors are administered to animals (e.g., mice, rats, dogs, cats and the like), disease model animals can be provided in which specified lesions including cancers are caused in the cranial nervous system.

Further, if the above mentioned structural genes code for peptides useful in the therapy for genetic diseases (e.g., Alzheimer disease, Parkinson's disease and the like), the therapy for the diseases can be performed by administering directly the recombinant vectors of the present invention to mammals (e.g., mice, rats, dogs, cats, human and the like), or by transplanting in the brains the cultured cells derived from the brains, which were transfected by the recombinant vectors.

The therapy for brain abscess can be performed by transfecting directly a recombinant vector assembled with a cancer-repressible gene as a structural gene to the tumor cells.

Furthermore, if the promoters of the present invention are found to be controlled by specified compounds in the cells of the cranial nervous system, and the specified compounds are administered so as to reach the brain in the body, the control ability of the specified compounds to promoter activity can be measured; thereby the compounds activate the promoter of the GIF (SEQ ID NO:3) gene to increase the produced amount of GIF, so that senile dementia of the Alzheimer type can be treated.

The above mentioned transformants can be tested for their control ability of the compounds to promoter activity by culturing the transformants in the presence of the specified compounds and by measuring the amount of gene products in the culture to compare with each amount.

The transformants are cultured by the methods which are publicly known in itself. Examples of mediums include MEM [Science, 122, 501 (1952)] supplemented with about 5 to 20% of fetal bovine serum, DMEM [Virology, 8, 396 (1959)], RPMI1640 medium [The journal of the American Medical Association, 199, 519 (1967)], 199 medium [Proceeding of the Society for the Biological Medicine, 73., 1 (1950)] and the like. Preferred pH is about 6 to 8. Culturing is usually performed at a temperature of about 30° C. to 40° C. for about 15 to 60 hours, if necessary, with aeration and stirring.

INDUSTRIAL APPLICABILITY

The substance of the present invention is applied to genetic diagnosis of Alzheimer disease, and thus expected to be available in the therapy for Alzheimer disease by transfecting the gene of interest into cells of the brain. Furthermore, the DNA coding for a protein (GIF) having growth-inhibitory action provides a transformant which enables to produce the protein using a genetic engineering technique. A large amount of GIF can be then produced by culturing the transformant. The GIF (SEQ ID NO:1) can be also used to develop therapeutic agents for the disease can be developed by using GIF promoters.

The present invention is illustrated in accordance with the following Examples.

EXAMPLE 1

Isolation and purification of the present substance

To 60 ml of water was added 20 g of gray matter of the normal human cerebral cortex, which was homogenized and centrifuged at 20,000 g for 1 hour to obtain a supernatant of 55 ml.

The resulting supernatant of 55 ml was subjected to ultrafiltration using an AMICON YM-10 membrane (trademark), and the obtained fractions containing substances having molecular weight of 10 kilodalton or more were applied on a DEAE-Sephacel column (1.6 cm φ×16 cm, Pharmacia Biosystems). The column was then washed with 200 ml of a washing buffer (20 mM Tris-HCl, pH 7.6, containing 50 mM NaCl), and eluted with 320 ml of 20 mM Tris-HCl (pH 7.6) having a linear concentration gradient of 50 mM to 300 mM NaCl. The chromatogram obtained using the above mentioned DEAE-Sephacel column is shown in FIG. 1. After fraction Nos 31 to 38 (40 ml) having inhibitive activity were collected to dialyze, the dialyzed solution was condensed with Ficol 400. The condensed solution was subjected to gel filtration using TSK G2000SW column (column size: 7.5 mm φ×6 cm; TOSO, CORPORATION) to collect fraction Nos 30 to 32 (2.5 ml) having the activity, and then the collected fractions dialyzed against 5 mM phosphate buffer (pH 7.4). The chromatogram obtained with gel filtration using the above mentioned TSK G2000SW is shown in FIG. 2. After the liquid volume was condensed down to 550 µl the solution was applied on C18 reverse-phase HPLC column (4.6 mm×25 cm, Senshu Chemistry Co., Ltd.). Elution was performed with a 5 mM ammonium formate solution having a linear gradient of 0% to 80% acetonitrile. The chromatogram obtained with C18 reverse-phase HPLC is shown in FIG. 3. As shown in FIG. 3, C18 reverse-phase HPLC substantially provided a single sharp peak, which demonstrates the isolation of the substance, GIF, (SEQ ID NO:1) of the present invention.

EXAMPLE 2

Determination of properties

The substance obtained in Example 1 was determined for the following various properties.

(1) Ultraviolet absorption spectrum

Three µg of the substance obtained in Example 1 in distilled water was determined for ultraviolet absorption spectrum using a Beckman DU65 spectrophotometer. The result is shown in FIG. 4.

(2) Stability

An aqueous solution having a concentration of 20 µg/ml of the substance obtained in Example 1 was prepared, and trifluoroacetic acid was added to 10 µl of the solution up to 0.1% at the final concentration (pH 3.0). The resulting solution was heated at 37° C. for 20 hours, then lyophilyzed. The resulting powder was dissolved to 10 µof Dulbecco's phosphate buffer (PBS(–)), and measured for inhibitive activity by the method described in the following Example 3, so that there was no decrease in the inhibitive activity. Further, 100 µl of 2 µg/ml aqueous solution of the substance obtained in Example 1 was heated at 37° C. for 20 hours or at 100° C. for 5 minutes. Then 10 µl of the solution was tested for stability in the same manner as in the above mentioned, so that there was no decrease in the inhibitive activity.

(3) Molecular weight

The substance (5 µg) obtained in Example 1 was dissolved in 10 µl of water was determined for molecular weight by sodium dodecyl sulfate (SDS) polyacrylamide having a gradient concentration of 7.5% to 20% gel electrophoresis (PAGE) using molecular weight markers, chymotrypsinogen A (molecular weight: 2,500), cytochrome C (molecular weight: 12,500) and Aprotinin (molecular weight: 6,500, BIO RAD), and thus its molecular weight was identified to be 5,000 dalton. The result is shown in FIG. 5.

Test Example: Measurement of growth-inhibitory action

In 6 mm microplate coated with gelatin-polyornithine were inoculated $1.7 \times 10^4$ cells which were prepared from the cerebral cortex of neonatal rats. Then, 100 µl of 125 µg/ml aqueous solution of the extract obtained from patients with Alzheimer disease by the same method as in Example 1 and 20 µl of the substance obtained in Example 1 were added to the MEMN 2 medium (modified Eagle's basal medium supplemented with insulin, transferrin, putrescine, progensterone and sodium selenite) without serum, and cultured in an incubator with 5% $CO_2$ at 37° C. for 5 days. The cells were fixed with paraformaldehyde and 90% methanol/5% acetic acid, then quantitated for MAP2 by ELISA using an antibody to microruble-binding protein 2 (MAP2) (Amersham). In contrast, only the extract obtained from patients with Alzheimer disease was added to the medium, which was cultured, and quantitated for MAP2. The inhibitive activity was expressed on the basis of the decreased rate (%) of the amount of MAP2.

The relationship between the amount of GIF and the inhibitive rate was determined by the above mentioned method. The result is shown in FIG. 6. As shown in FIG. 6, the inhibitive activity reached equilibrium at the GIF concentration of 0.2 µg/ml, retaining about 90%.

EXAMPLE 3

Analysis of amino acid sequence

Two hundred μg of the substance obtained in Example 1 was pyridylethylated by the conventional method. Fifty μg of the pyridylethylated substance was cleaved with cyanogen bromide. The pyridylethylated substance was dissolved in 100 μl of 0.1 M Tris-HCl (pH 8.0) solution, to which 0.5 μg of N-tosyl-L-phenylalanyl chloromethyl ketone (TPCK)-trypsin (Sigma), or endoproteinase Asp-N (Boeringer) or S. aureus V8 protease (Sigma) was added, and then the solution was reacted at 37° C. for 5 hours. Peptide fragments obtained by these four methods was each separated by C18 reverse-phase HPLC (0–80% acetonitrile/0.1% trifluoroacetic acid), and then the obtained fractions were subjected to analysis using a 477A protein sequenator (Applied Biosystems). The retention time of the resulting peak was compared with that of the standard substance to determine the entire amino acid sequence. As a result, GIF was found to have the same entire amino acid sequence as in the above mentioned.

EXAMPLE 4

Isolation of the present gene

On the basis of the amino acid sequence of GIF (SEQ ID NO:1) extracted from the human brain, two oligonucleotides of 5'ATGGATCCCGAGACCTGCCC (SEQ ID NO:7) and 5'CTGGCAGCAGCAGCTGCACTTTCTC (SEQ ID NO:8) were synthesized. After cDNA was prepared from mRNA, which was obtained from the human brain using these primers, with reverse transcriptase, the cDNA was subjected to the polymerase chain reaction. The resulting product was subcloned into a plasmid vector pUC 19, and determined for the base sequence as mentioned above. The sequence was identified as the same amino acid sequence as the above mentioned GIF (SEQ ID NO:1).

Using cDNA library prepared against mRNA in normal human cerebrum, 1×106 clones were grown on a plate to transfer on a nitrocellulose membrane. A probe in which the subcloned oligonucleotide was labeled with $^{32}$p was prepared, and reacted in a hybridization solution containing 50% formamide and 5×SSC (0.15 M NaCl and 0.15 M sodium citrate, pH 7.0) at 42° C. for 18 hours to make the probe hybridized on the nitrocellulose membrane, and then the filter was washed. Finally, the nitrocellulose membrane was subjected to autoradiography in 0.1×SSC (0.15 M NaCl and 15 mM sodium citrate, pH 7.0) at 55° C. to isolate 24 cDNA specific for the above mentioned prove. Determination of base sequences of these cDNA revealed that there was the base sequence coding for 68 amino acids (FIG. 8).

EXAMPLE 5 mRNAs were extracted from the brain of a normal subject and that of a patient with Alzheimer disease, respectively, 2 μg of which was each electrophoresed in alkaline denaturated agarose gel. The electrophoresed mRNA was then transferred to a nitrocellulose membrane, and hybridized in a hybridization solution using cDNA (SEQ ID NO:4) as a probe at 42° C. for 18 hours, and then the filter was washed. Finally, the nitrocellulose membrane was washed with 0.1× SCC and 0.1% SDS and subjected to autoradiography at 42° C. for 18 hours. As a result, mRNA having about 500 bp was observed in the both brains from patients with Alzheimer disease and normal subjects, but the amount of the mRNA was found to be decreased in the patients with Alzheimer disease (FIG. 7).

EXAMPLE 6

Cloning of human GIF genomic DNA A cosmid human genomic DNA library (pWE15) was screened using cDNA of human GIF as a probe. The reaction was performed in a solution of 5×SSC, 1×denhalt's, 10% dextran sulfate, 50% formamide and 20 mM sodium phosphate at 42° C. for 18 hours. After the reaction, the filter was washed twice with 2×SSC at a room temperature for 15 min and washed twice with a solution of 0.1×SCC and 0.1% SDS at a temperature of 55° C. for 15 min, and then the washed filter was subjected to autoradiography to search for cosmids which react with the probe. As a result, a positive clone was obtained, and thus it was indicated that a DNA integrated to the cosmid hybridized with the probe by Southern blot hybridization. Then the entire base sequence of the DNA fragment (about 35 Kb) was determined, so that the genomic DNA of GIF shown in FIG. 9 had the exon-intron structure, and the ends of the exon and intron had the base sequence shown in FIG. 9. Further, the upstream region of the cDNA (exon 1) was found to be the human GIF promoter region and to have the base sequence shown in FIG. 10.

EXAMPLE 7

Expression of human GIF in *Escherichia coli*

NcoI and HindIII restriction fragments were individually transfected into the upstream (ATG upstream) and downstream regions of the region coding for GIF of human GIF cDNA (SEQ ID NO:4) obtained from Example 4 by the PCR method using primers having NcoI and HindIII restriction site, respectively. Then, the human GIF cDNA was cleaved with NcoI and HindIII, and the resulting DNA fragments integrated to the NcoI-HindIII restriction site of a plasmid pKK233-2 (Pharmacia Biosystems) (FIG. 11). The plasmid for expressing GIF was transfected into *Escherichia coli* JM 105 strain to select AMP$^r$ strain. The selected *Escherichia coli* strain was then cultured in a medium, to which isopropyl-β-D-thiogalactoside (IPTG) was added up to 1 mM on the initiation of logarithmic growth phase of the bacterium, with additional culture for 5.5 hours. A crude extract was obtained from the collected bacteria by ultrasonification and the following centrifugation, and purified by the similar method to that in Example 1 to obtain human recombinant GIF.

EXAMPLE 8

Growth-inhibitory action of human recombinant GIF

Growth-inhibitory action of human recombinant GIF obtained in Example 7 was measured by the method described in Example 2. As a result, the human recombinant GIF was found to have the inhibitive activity of about 0.1 time that of the naturally occurring human GIF (FIG. 12).

BRIEF DESCRIPTION OF DRAWINGS

FIG. 4 is a ultraviolet absorption spectrum of GIF (SEQ ID NO:1)

FIG. 5 shows a SDS-PAGE pattern of GIF (SEQ ID NO:1).

FIG. 8 shows the base sequence (SEQ ID NO:4) and amino acid sequence (SEQ ID NO:1) of the cDNA coding for GIF.

FIG. 9 shows the base sequence of the exson-intron structure in the genomic DNA for GIF Intron 1 is identified as SEQ ID NO:5 and Intron 2 SEQ ID NO:6.

FIG. 10 shows the base sequence of the GIF promoter region (SEQ ID NO:3).

Figure 1:
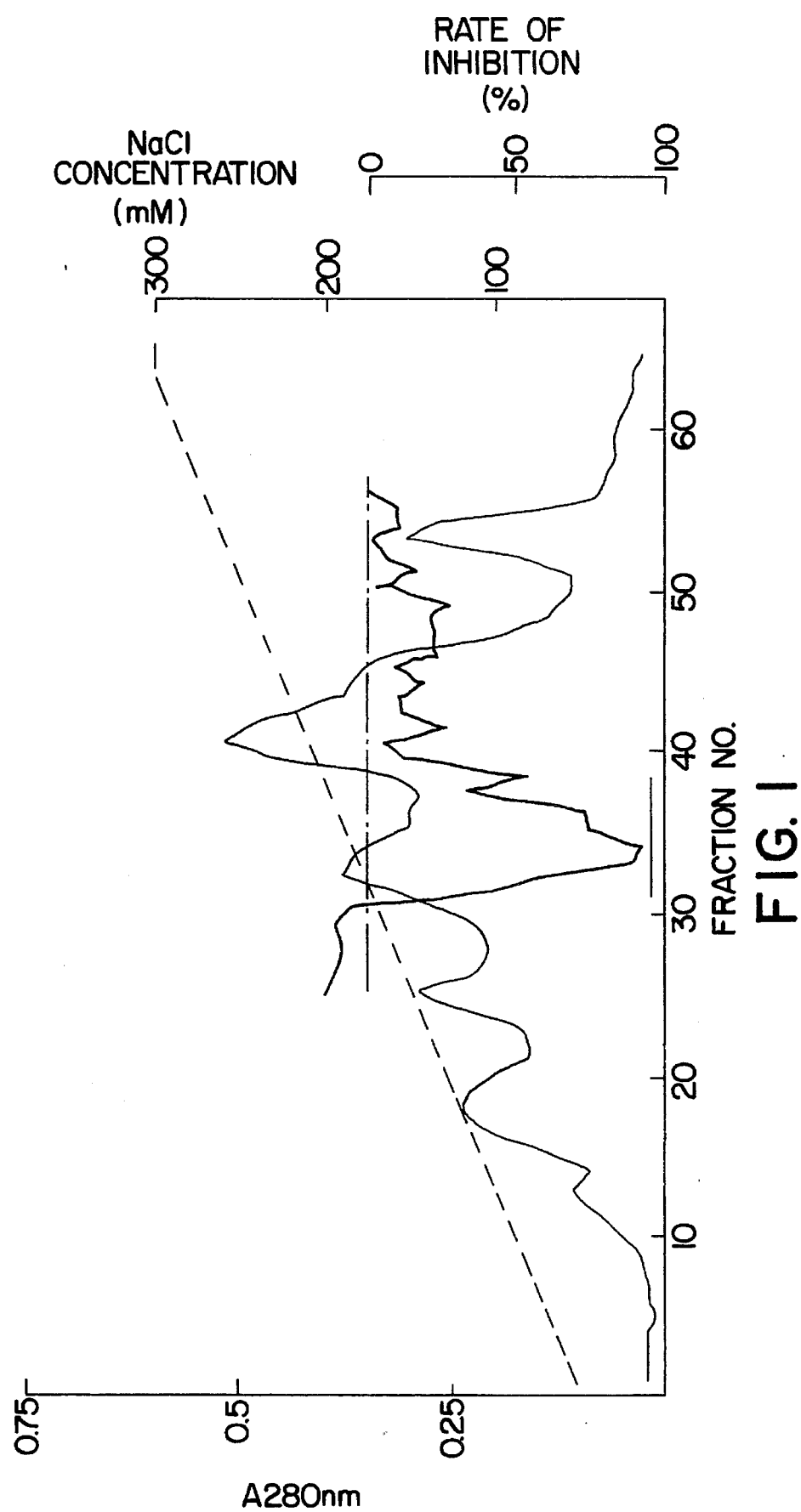
FIG. 1 is a chromatogram of the fractions containing substances having molecular weight of 10 kilodalton or more which were applied on a DEAE-Sephacel column.
Figure 2:
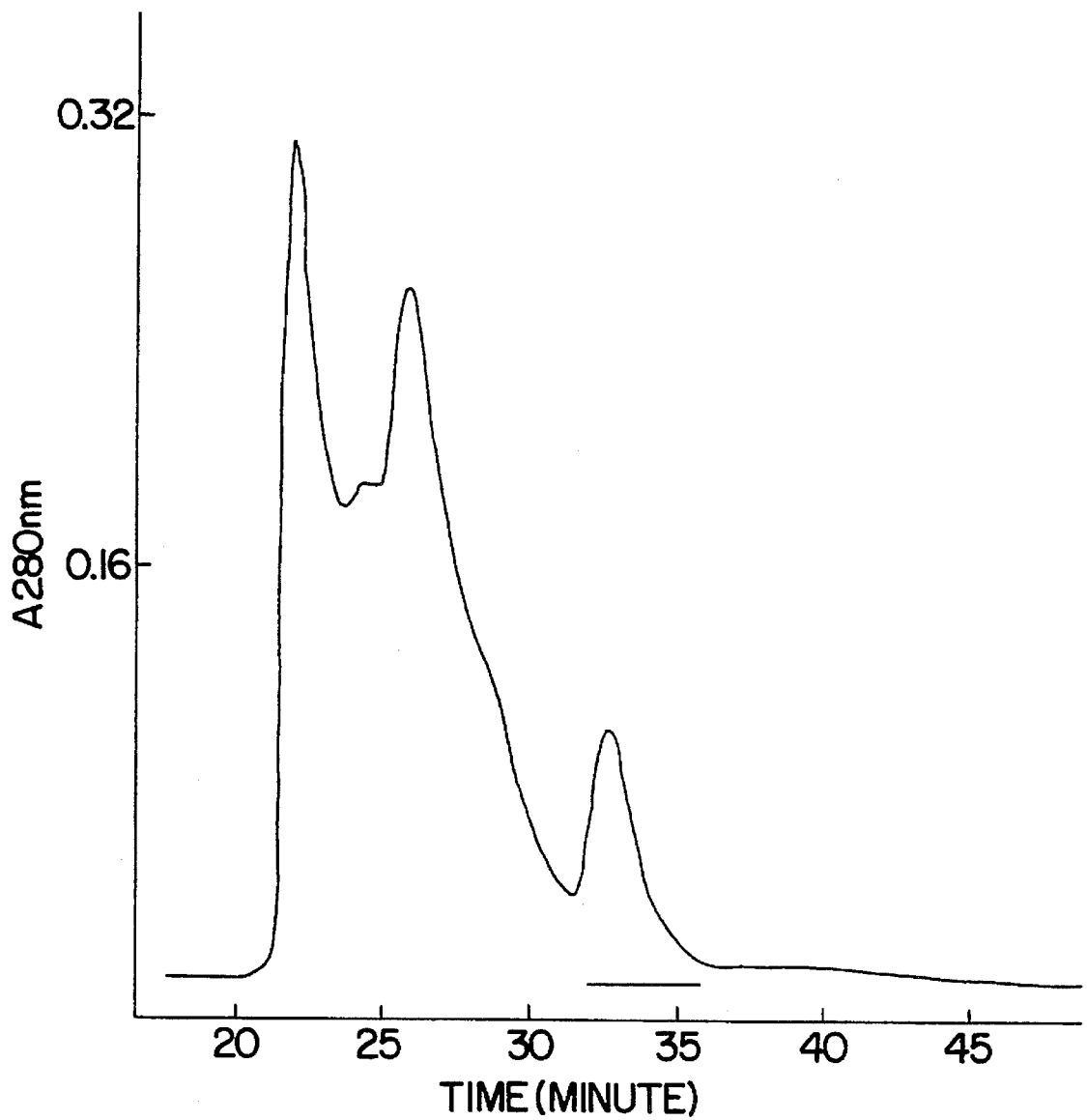
FIG. 2 is a chromatogram where fractions having growth-inhibitory action were subjected to gel filtration.
Figure 3:
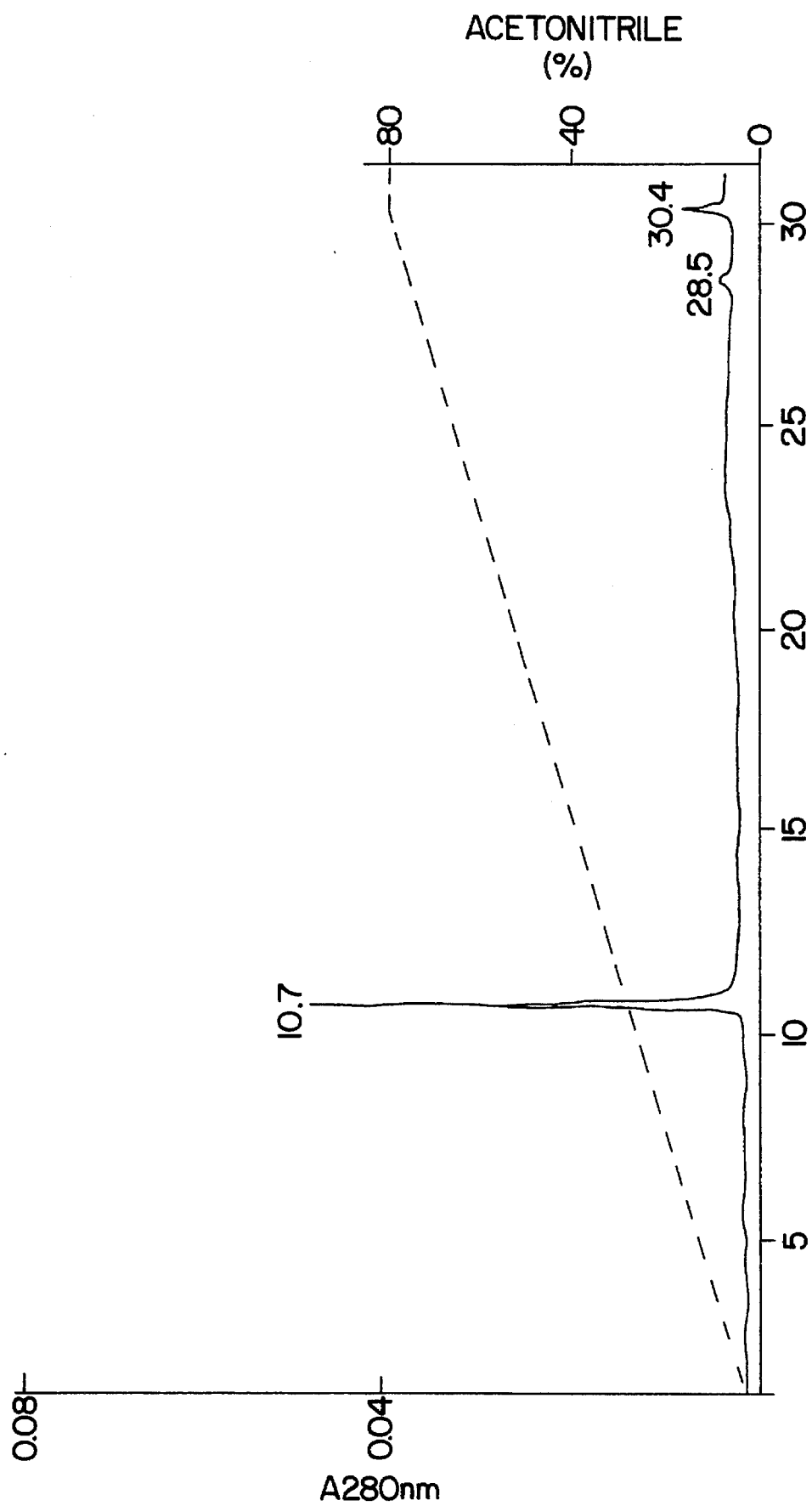
FIG. 3 is a chromatogram where GIF (SEQ ID NO:1) was subjected to C18 reverse-phase HPLC.
Figure 7:
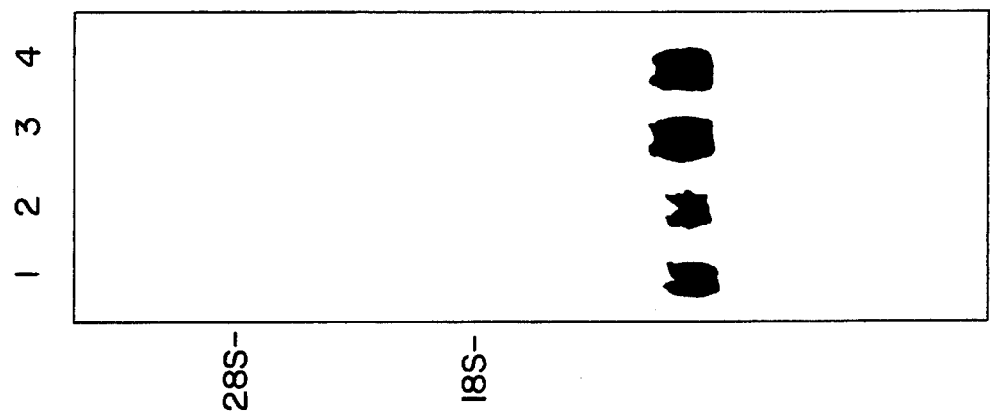
FIG. 7 is a chromatogram which shows the results of Southern blot analysis using cDNA (SEQ ID NO:4) for GIF (SEQ ID NO:4) as a probe. This shows that the amount of mRNA for the growth-inhibitory factor from patients with Alzheimer disease (1 and 2) is more decreased than that from normal subjects (3 and 4).
Figure 6:
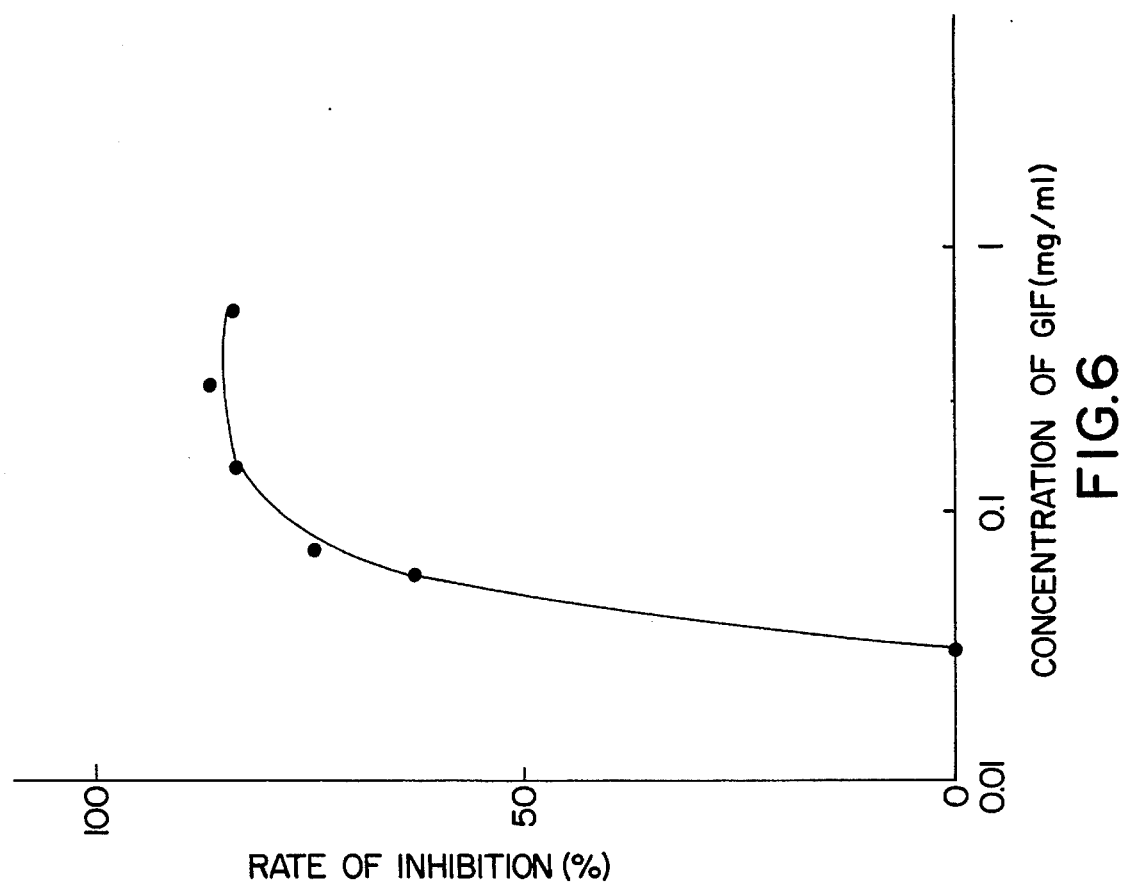
FIG. 6 is a graph of the relationship between the amount of GIF (SEQ ID NO:1) and the nutritional activity-inhibitive rate on nerve.
Figure 11:
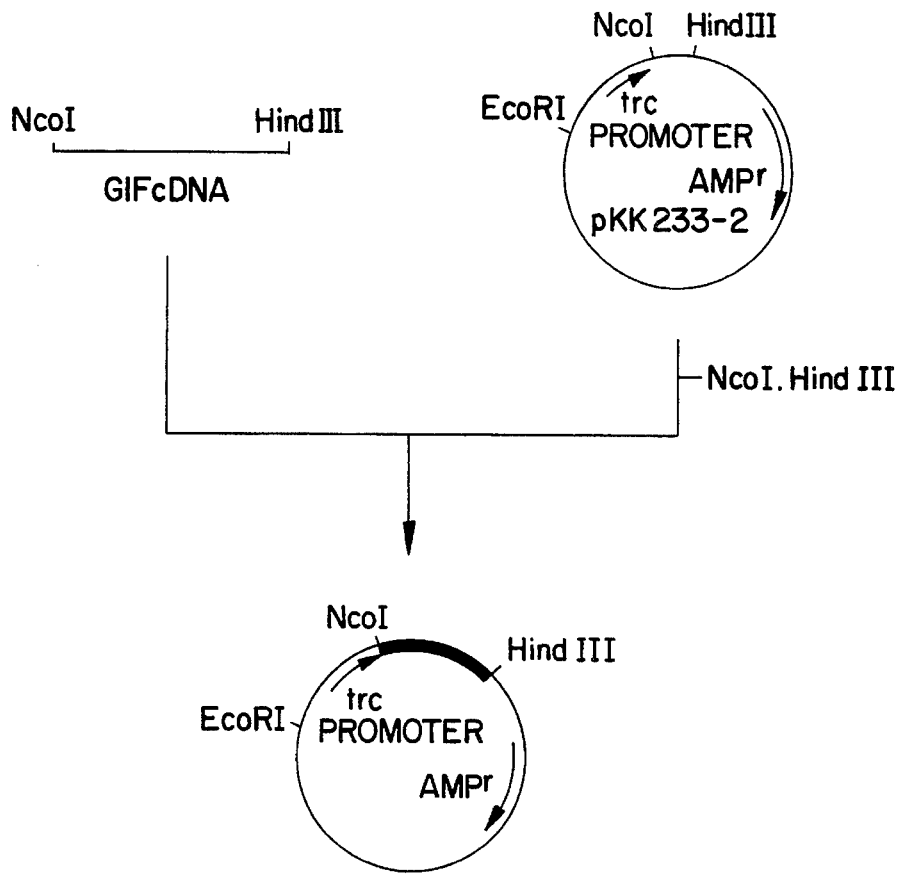
FIG. 11 is a diagram representing the construction of the plasmid for expressing GIF.
Figure 12:
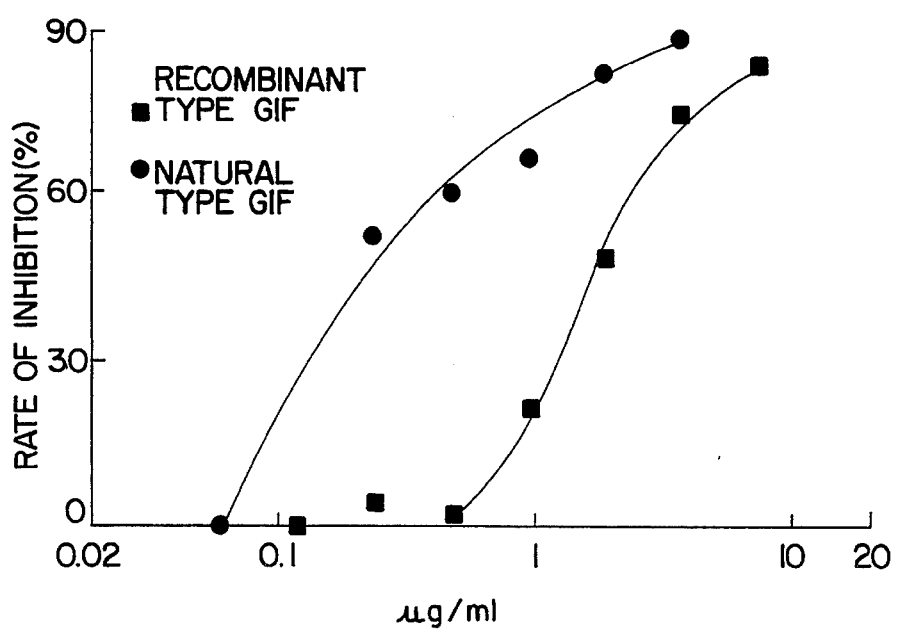
FIG. 12 is a graph representing growth-inhibitory action of the recombinant GIF.

We claim:

1. A recombinant DNA coding for a protein having growth-inhibitory action (GIF) wherein said protein has the following amino acid sequence: (SEQ ID NO:1)

| Met 1 | Asp | Pro | Glu | Thr 5 | Cys | Pro | Cys | Pro | Ser 10 |
|---|---|---|---|---|---|---|---|---|---|
| Gly | Gly | Ser | Cys | Thr 15 | Cys | Ala | Asp | Ser | Cys 20 |
| Lys | Cys | Glu | Gly | Cys 25 | Lys | Cys | Thr | Ser | Cys 30 |
| Lys | Lys | Ser | Cys | Cys 35 | Ser | Cys | Cys | Pro | Ala 40 |
| Glu | Cys | Glu | Lys | Cys 45 | Ala | Lys | Asp | Cys | Val 50 |
| Cys | Lys | Gly | Gly | Glu 55 | Ala | Ala | Glu | Ala | Glu 60 |
| Ala | Glu | Lys | Cys | Ser 65 | Cys | Cys | Gln 68 | | |

2. The DNA as claimed in claim 1 wherein the DNA coding for GIF has the following base sequence: (SEQ ID NO:2)

| ATG GAC CCT GAG ACC TGC CCC TGC CCT TCT GGT GGC TCC TGC ACC TGC | 48 |
| GCG GAC TCC TGC AAG TGC GAG GGA TGC AAA TGC ACC TCC TGC AAG AAG | 96 |
| AGC TGC TGC TCC TGC TGC CCT GCG GAG TGT GAG AAG TGT GCC AAG GAC | 144 |
| TGT GTG TGC AAA GGC GGA GAG GCA GCT GAG GCA GAA GCA GAG AAG TGC | 192 |
| AGC TGC TGC CAG | 204 |

3. A recombinant vector containing the DNA according to claim 1.

4. A transformant cell carrying the vector according to claim 3.

5. A method for preparing GIF wherein the transformant according to claim 4 is cultured in a medium.

6. The recombinant vector according to claim 3 wherein the DNA is coupled to the coupled to the downstream of a promoter region having the following sequence (SEQ ID NO:3)

| GAATTCTAGA | ATGAAGGGA | AGAGAGGCAG | GGAAGAGCTG | GGAAATACGC | AAAGCGCCTT |
| TTTCTCCACT | TTCGGAGATG | GTACGTGCGC | GCTTCCACGC | AGTGGCGGCT | GCTGCGGCGA |
| GCACGTCCCT | GCGGGACCCA | CGCGGCCAGT | GGGCTGGCAG | TCGCGGGATA | GCGGCGGCGA |
| GTGGGTCGTG | CACGCGGATC | CGGGGTCCA | GTGGGGGCGC | ACGCGCGGGC | GTGGGCGAGC |
| GGGCCCCGGC | AGTGCACACA | CACGGCAGGG | GCGGGGCGAC | AGATGCAGTC | GTGCGCCGGA |
| GCCCAAGCGC | ACAAACGGAA | AGAGCGGCCG | GTGGCGCAGG | GGCGGGCCC | AGCGGGCTTG |
| GCATGCGCGC | CCCCGCCCGA | GGCTATAAAA | GCATCGCCAC | CTGCTGCCAC | TAGCCAAGCC |
| GCGCGT | | | | | |

7. A transformant cell carrying the recombinant vector according to claim 6.

8. A recombinant DNA having a promoter region of the GIF gene promoter region (SEQ ID NO:3) has the following base sequence

| GAATTCTAGA | ATGAAGGGGA | AGAGAGGGAG | GGAAGAGCTG | GGAAATACGC | AAAGCGCCTT |
| TTTCTCGACT | TTCGGAGATG | GTACGTGCGC | GCTTCGACGG | AGTGGCGGCT | GCTGCGGCGA |
| GCACGTCCCT | GCGGGACCCA | CGCGGGCAGT | GGGCTGGCAG | TCGCGGGATA | GCGGCGGGGA |
| GTGGGTCGTG | CACGCGGATG | CGGGGTCCCA | GTGGGGGCGC | ACGCGCGGGG | GTGGGCGAGC |
| GGGCCCCGGC | AGTGCACACA | CACGGCAGGG | GCGGGGCGAC | AGATGCAGTC | GTGCGCCGGA |
| GCCCAAGCGC | ACAAACGGAA | AGAGCGGCCG | GTGGGGGAGG | GGCGGGCCCC | AGCGGGGTTG |
| GCATGCGCGC | CCCCGCCCGA | GGCTATAAAA | CCATCGCCAC | CTGCTGCCAC | TAGCCAAGGG |
| GCGCGT. | | | | | |

9. A recombinant vector containing the recombinant DNA according to claim 8.

10. A transformant cell carrying the recombinant vector according to claim 9.

\* \* \* \* \*